US009655567B2

(12) United States Patent
Takanaka et al.

(10) Patent No.: US 9,655,567 B2
(45) Date of Patent: May 23, 2017

(54) RADIATION DIAGNOSTIC APPARATUS, X-RAY COMPUTED TOMOGRAPHY APPARATUS, AND IMAGE PROCESSING METHOD

(75) Inventors: Makoto Takanaka, Nasushiobara (JP); Takuya Sakaguchi, Shioya-gun (JP); Masanori Matsumoto, Nasushiobara (JP); Masaki Kobayashi, Otawara (JP); Satoshi Yamashita, Nasushiobara (JP); Shumpei Oohashi, Otawara (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 462 days.

(21) Appl. No.: 12/696,478

(22) Filed: Jan. 29, 2010

(65) Prior Publication Data
US 2010/0202675 A1 Aug. 12, 2010

(30) Foreign Application Priority Data

Feb. 6, 2009 (JP) .................................. 2009-025882
Dec. 14, 2009 (JP) .................................. 2009-283207

(51) Int. Cl.
*G06K 9/00* (2006.01)
*A61B 6/03* (2006.01)
*A61B 6/00* (2006.01)
(52) U.S. Cl.
CPC .............. *A61B 6/032* (2013.01); *A61B 6/405* (2013.01); *A61B 6/482* (2013.01)

(58) Field of Classification Search
CPC ............ A61B 6/032; A61B 2019/5238; A61B 6/5247; A61B 8/0825; G01N 23/046;
(Continued)

(56) References Cited

U.S. PATENT DOCUMENTS 4,544,949 A * 10/1985 Kurihara .............. H04N 5/3205
348/E5.089
5,008,947 A 4/1991 Yamada
(Continued)

FOREIGN PATENT DOCUMENTS

CN  101237819 A  8/2008
CN  101249000 A  8/2008
(Continued)

OTHER PUBLICATIONS

Chinese Office Action issued Feb. 13, 2012, in Patent Application No. 201010112971.7.
(Continued)

*Primary Examiner* — Reginald R Reyes
(74) *Attorney, Agent, or Firm* — Oblon, McClelland, Maier & Neustadt, L.L.P.

(57) ABSTRACT

An X-ray image generating unit alternately generates X-ray images each obtained by radiating X-rays having a higher level of energy and X-ray images each obtained by radiating X-rays having a lower level of energy. Further, every time an X-ray image has been generated by the X-ray image generating unit, a dual energy subtraction image generating unit generates a dual energy subtraction image by using the X-ray image that has just been generated and the X-ray image generated immediately preceding the X-ray image.

20 Claims, 10 Drawing Sheets

(58) Field of Classification Search
CPC . G06T 2207/20224; G06T 2207/10116; G06T 2207/10121
USPC .......................................................... 382/130
See application file for complete search history.

(56) References Cited

U.S. PATENT DOCUMENTS

| | | | |
|---|---|---|---|
| 7,110,500 B2 * | 9/2006 | Leek .................. | H05G 1/58 378/106 |
| 2004/0071265 A1 * | 4/2004 | Maschke ............ | H04N 5/3205 378/98.11 |
| 2005/0096537 A1 * | 5/2005 | Parel et al. ................ | 600/427 |
| 2008/0309783 A1 * | 12/2008 | Nozaki .................. | G06T 5/006 348/222.1 |
| 2009/0180595 A1 * | 7/2009 | Spahn ................ | A61B 6/4233 378/197 |

FOREIGN PATENT DOCUMENTS

| | | |
|---|---|---|
| JP | 2-63439 | 3/1990 |
| JP | 7-148155 | 6/1995 |
| JP | 2003-298939 | 10/2003 |
| JP | 2004-105643 | 4/2004 |
| JP | 2005-270201 | 10/2005 |
| JP | 2007-195633 | 8/2007 |
| JP | 2008-73115 | 4/2008 |
| JP | 2008-284081 | 11/2008 |
| JP | 2009-131464 | 6/2009 |
| WO | WO 2007/086369 A1 | 8/2007 |

OTHER PUBLICATIONS

Office Action issued Apr. 14, 2011 in China Application No. 201010112971.7.
Japanese Office Action issued Oct. 8, 2013, in Japan Patent Application No. 2009-283207 (with English translation).

* cited by examiner

RADIATION DIAGNOSTIC APPARATUS, X-RAY COMPUTED TOMOGRAPHY APPARATUS, AND IMAGE PROCESSING METHOD

CROSS-REFERENCE TO RELATED APPLICATIONS

This application is based upon and claims the benefit of priority from the prior Japanese Patent Application No. 2009-025882, filed on Feb. 6, 2009, and No. 2009-283207, filed on Dec. 14, 2009; the entire contents of which are incorporated herein by reference.

BACKGROUND OF THE INVENTION

1. Field of the Invention

The present invention generally relates to a radiation diagnostic apparatus, an X-ray computed tomography apparatus, and an image processing method for radiating radiation rays onto an examined subject and generating an image by detecting radiation rays that have passed through the examined subject. The present invention specifically relates to generating a subtraction image by performing a dual energy subtraction process.

2. Description of the Related Art

As a method for treating the coronary arteries of the heart, a method called Percutaneous Coronary Intervention (PCI) is conventionally known. PCI is a method by which a catheter is inserted into a blood vessel of an examined subject (hereinafter, the "subject") so that stenosed parts or obstructed parts of the coronary arteries can be expanded by using the inserted catheter. When performing a PCI, doctors bring a catheter to the location of a lesion in the coronary arteries while looking at an X-ray image taken by an X-ray diagnostic apparatus.

Further, according to a commonly-used PCI method, a contrast agent is administered to the subject so that an X-ray image can be taken by performing Digital Angiography (DA) or Digital Subtraction Angiography (DSA). DA is an image taking method used for generating an image in which blood vessels are highlighted by a contrast agent by performing digital processing. DSA is an image taking method used for generating an image in which the picture contrast of only the blood vessels is enhanced by defining an image obtained before a contrast agent is administered to the subject as a "mask image" and applying a subtraction process to the mask image and to another image obtained after the contrast agent is administered to the subject (see, for example, JP-A 2007-195633 (KOKAI)).

When an image taking method such as DA or DSA described above is used, although the image in which the blood vessels are highlighted can be generated, other sites (e.g., bones) that are not necessary in the diagnosing process are also shown in the image while overlapping the blood vessels. As a result, in some situations, it is difficult to see the movement of the heart muscles, which need to be looked at in treatments using PCI.

To cope with this problem, in recent years, an image taking method called "dual energy subtraction", which utilizes the fact that different sites have different X-ray absorption rates, has been used. The dual energy subtraction method is an image taking method by which two sets of X-rays having mutually different levels of energy are alternately radiated onto a site that is a target of the image taking process so that a subtraction process can be applied to the obtained X-ray images. When such a dual energy subtraction method is used, it is possible to obtain an image from which the sites that are not necessary in the diagnosing process are eliminated or an image in which the contrast agent or a stent is highlighted. In the following sections, an image that is obtained by performing a subtraction process will be referred to as a "subtraction image".

The conventional technique described above, however, has a problem where it is not possible to efficiently generate the subtraction images by performing the dual energy subtraction process in relation to the number of times the X-rays are radiated.

More specifically, according to a commonly-used dual energy subtraction method, a subtraction image used in a diagnosing process is generated by applying a subtraction process to an odd-numbered-frame image that has been taken as a (2m−1)'th image and an even-numbered-frame image that has been taken as a 2m'th image (where m is a natural number). For example, the frame rate at which the images are taken is expressed as "fr1" (images per second), the frame rate at which the images generated through the subtraction process are displayed can be expressed as "fr1"/2 (images per second). In other words, according to the conventional dual energy subtraction method, it is possible to obtain only half as many processed images as the number of times the X-rays are radiated.

SUMMARY OF THE INVENTION

According to one aspect of the present invention, a radiation diagnostic apparatus includes a radiation radiating unit that alternately radiates radiation rays having a first level of energy and radiation rays having a second level of energy that is different from the first level of energy onto a subject; a radiation detecting unit that detects radiation rays that have passed through the subject; an image generating unit that generates a first image based on the radiation rays that have been detected by the radiation detecting unit when the radiation rays having the first level of energy were radiated and generates a second image based on the radiation rays that have been detected by the radiation detecting unit when the radiation rays having the second level of energy were radiated; and a subtraction image generating unit that, every time the first image or the second image has been generated by the image generating unit, generates a subtraction image by using the first image or the second image that has just been generated and the image generated immediately preceding the first image or the second image.

According to another aspect of the present invention, an X-ray computed tomography apparatus includes an X-ray radiating unit that alternately radiates X-rays having a first level of energy and X-rays having a second level of energy that is different from the first level of energy onto a subject from mutually different projection directions; an X-ray detecting unit that detects X-rays that have passed through the subject; a projection data generating unit that generates a piece of first projection data based on the X-rays that have been detected by the X-ray detecting unit when the X-rays having the first level of energy were radiated and generates a piece of second projection data based on the X-rays that have been detected by the X-ray detecting unit when the X-rays having the second level of energy were radiated; a difference data generating unit that, every time the piece of the first projection data or the piece of the second projection data has been generated by the projection data generating unit, generates a piece of difference data corresponding to a difference between the piece of the first projection data or the piece of the second projection data that has just been generated and the piece of projection data generated immediately preceding the piece of the first projection data or the piece of the second projection data; and an image reconstruction processing unit that reconstructs an image from the pieces of difference data that have been generated by the difference data generating unit.

According to still another aspect of the present invention, an image processing method includes alternately radiating radiation rays having a first level of energy and radiation rays having a second level of energy that is different from the first level of energy onto a subject; detecting radiation rays that have passed through the subject; generating a first image based on the radiation rays that have been detected when the radiation rays having the first level of energy were radiated and generating a second image based on the radiation rays that have been detected when the radiation rays having the second level of energy were radiated; and generating, every time the first image or the second image has been generated, a subtraction image by using the first image or the second image that has just been generated and the image generated immediately preceding the first image or the second image.

According to still another aspect of the present invention, an image processing method comprising: alternately radiating X-rays having a first level of energy and X-rays having a second level of energy that is different from the first level of energy onto a subject from mutually different projection directions; detecting X-rays that have passed through the subject; generating a piece of first projection data based on the X-rays that have been detected when the X-rays having the first level of energy were radiated and generating a piece of second projection data based on the X-rays that have been detected when the X-rays having the second level of energy were radiated; generating, every time the piece of the first projection data or the piece of the second projection data has been generated, a piece of difference data corresponding to a difference between the piece of the first projection data or the piece of the second projection data that has just been generated and the piece of projection data generated immediately preceding the piece of the first projection data or the piece of the second projection data; and reconstructing an image from the pieces of difference data that have been generated.

DETAILED DESCRIPTION OF THE PREFERRED EMBODIMENTS

Exemplary embodiments of a radiation diagnostic apparatus, an X-ray computed tomography apparatus, and an image processing method according to the present invention will be explained in detail, with reference to the accompanying drawings.

First, an example in which the present invention is applied to an X-ray diagnostic apparatus will be explained as a first embodiment of the present invention. In the first embodiment, an image that is generated by performing a dual energy subtraction process will be referred to a "dual energy subtraction image". Further, an image that is generated by performing a DSA process will be referred to as a "DSA image".

Figure 1:
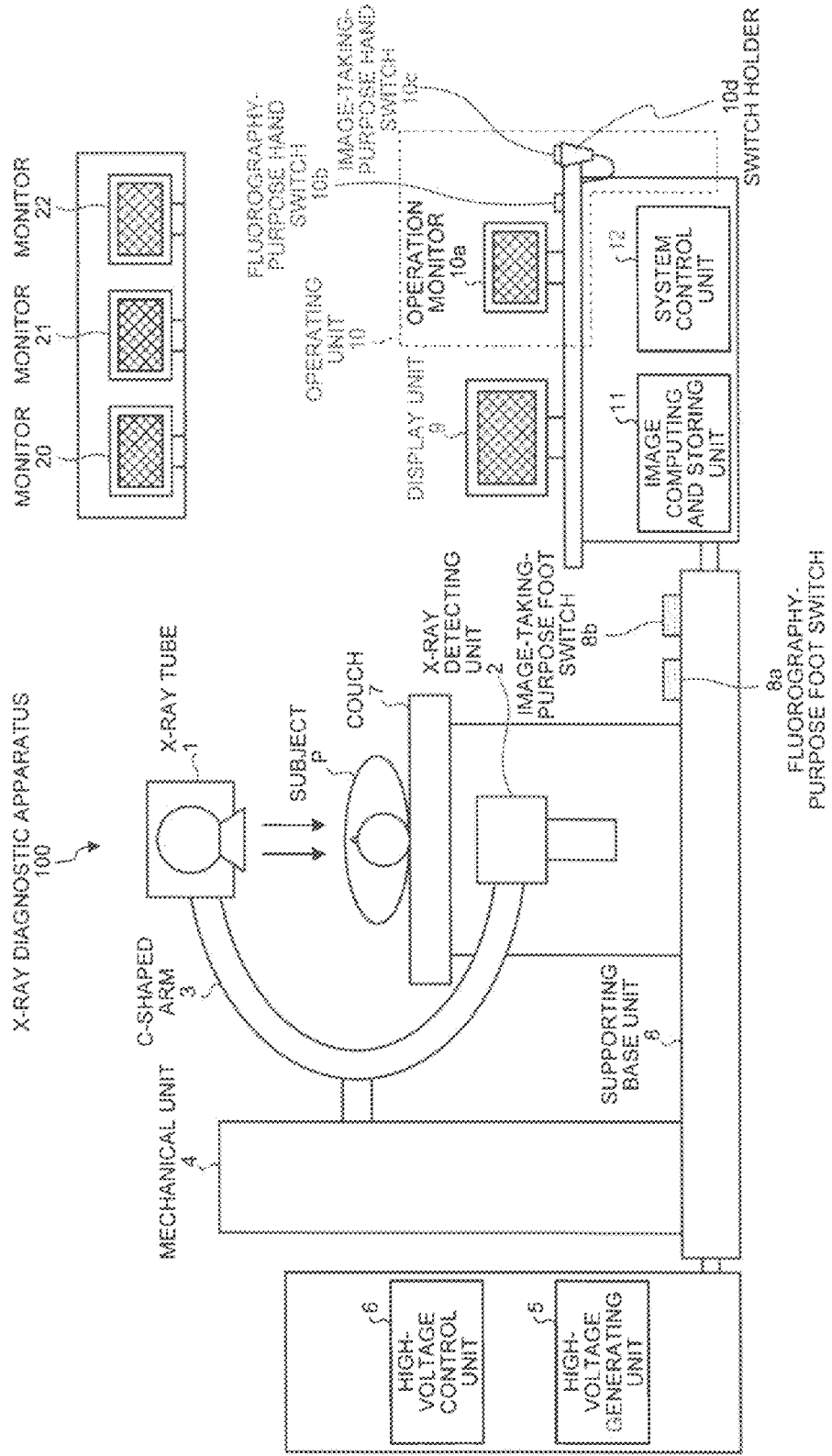
FIG. 1 is a block diagram of an X-ray diagnostic apparatus according to a first embodiment of the present invention.

To begin with, a configuration of an X-ray diagnostic apparatus according to the first embodiment will be explained. FIG. 1 is a block diagram of an X-ray diagnostic apparatus 100 according to the first embodiment. As shown in FIG. 1, the X-ray diagnostic apparatus 100 includes an X-ray tube 1, an X-ray detecting unit 2, a C-shaped arm 3, a mechanical unit 4, a high-voltage generating unit 5, a high-voltage control unit 6, a couch 7, a gantry unit 8, a display unit 9, an operating unit 10, an image computing and storing unit 11, a system control unit 12, and monitors 20 to 22.

The X-ray tube 1 generates X-rays by using a high voltage supplied by the high-voltage generating unit 5 and radiates the generated X-rays onto an examined subject (hereinafter, "subject") P.

The X-ray detecting unit 2 detects X-rays that have passed through the subject P. The X-ray detecting unit 2 may be configured with, for example, a Flat Panel Detector (FPD) or an Image Intensifier (I. I.).

The C-shaped arm 3 holds the X-ray tube 1 and the X-ray detecting unit 2. More specifically, the C-shaped arm 3 is shaped like the letter "C" so that the X-ray tube 1 is supported at one end thereof, while the X-ray detecting unit 2 is supported at the other end thereof. In the present example, the C-shaped arm 3 is configured so as to support the X-ray tube 1 and the X-ray detecting unit 2 in such a manner that the X-ray tube 1 and the X-ray detecting unit 2 oppose each other while the subject P is interposed therebeteween.

The mechanical unit 4 supports the C-shaped arm 3 and is also operable to rotate or move the C-shaped arm 3.

The high-voltage generating unit 5 supplies the high voltage that is required by the X-ray tube 1 to generate the X-rays.

The high-voltage control unit 6 controls the process to generate the high-voltage performed by the high-voltage generating unit 5. Due to the control exercised by the high-voltage control unit 6 over the high-voltage generating process, it is possible to change the dose of the X-rays radiated from the X-ray tube 1 onto the subject P.

The couch 7 includes a top plate on which the subject P can be placed and a foot part that supports the top plate. The top plate is configured so as to be movable in vertical and horizontal directions.

The gantry unit 8 supports the mechanical unit 4, the couch 7, and the like. A fluorography-purpose foot switch 8a and an image-taking-purpose foot switch 8b are provided on the gantry unit 8. The fluorography-purpose foot switch 8a is used by an operator to instruct that an image taking process performed with a fluorography setting should be started or ended. The image-taking-purpose foot switch 8b is used by the operator to instruct that an image taking process performed with an image-taking setting should be started or ended.

The display unit 9 displays, for example, various images that are generated by the image computing and storing unit 11. The display unit 9 may be configured with, for example, a Flat Panel Display (FPD) device or a Cathode Ray Tube (CRT) display device.

The operating unit 10 receives various operations from the operator. The operating unit 10 includes an operation monitor 10a, a fluorography-purpose hand switch 10b, an image-taking-purpose hand switch 10c, and a switch holder 10d. The operation monitor 10a displays information related to operations of the X-ray diagnostic apparatus 100, such as information of the patient, the conditions under which images are taken, and image-taking protocols. The fluorography-purpose hand switch 10b is used by the operator to instruct that an image taking process performed with a fluorography setting should be started or ended. The image-taking-purpose hand switch 10c is used by the operator to instruct that an image taking process performed with an image-taking setting should be started or ended. The switch holder 10d is used to fix the image-taking-purpose hand switch 10c onto an operation desk or the like.

The image computing and storing unit 11 generates various images based on the X-rays that have been detected by the X-ray detecting unit 2. Further, the image computing and storing unit 11 includes a storage means such as a Hard Disk Drive (HDD) and stores therein the various images that have been generated.

The system control unit 12 exercises overall control of the X-ray diagnostic apparatus 100 by controlling the functional elements described above, based on operations performed by the operator.

The monitors 20 to 22 display, for example, the various images that have been generated by the image computing and storing unit 11. The monitors 20 to 22 may be configured with, for example, Flat Panel Display (FPD) devices and/or Cathode Ray Tube (CRT) display devices that are positioned side by side.

The configuration of the X-ray diagnostic apparatus 100 according to the first embodiment has thus been explained. In the X-ray diagnostic apparatus 100 according to the first embodiment that is configured as described above, the image computing and storing unit 11 alternately generates X-ray images each obtained by radiating X-rays having a first level of energy and X-ray images each obtained by radiating X-rays having a second level of energy that is different from the first level of energy. Further, every time an X-ray image has been generated, the image computing and storing unit 11 generates a dual energy subtraction image by using the X-ray image that has just been generated and the X-ray image generated immediately preceding the X-ray image. With this arrangement, according to the first embodiment, it is possible to efficiently generate the subtraction image by performing the dual energy subtraction process.

In the following sections, functions of the image computing and storing unit 11 and the system control unit 12 that are described above will be explained further in detail.

Figure 2:
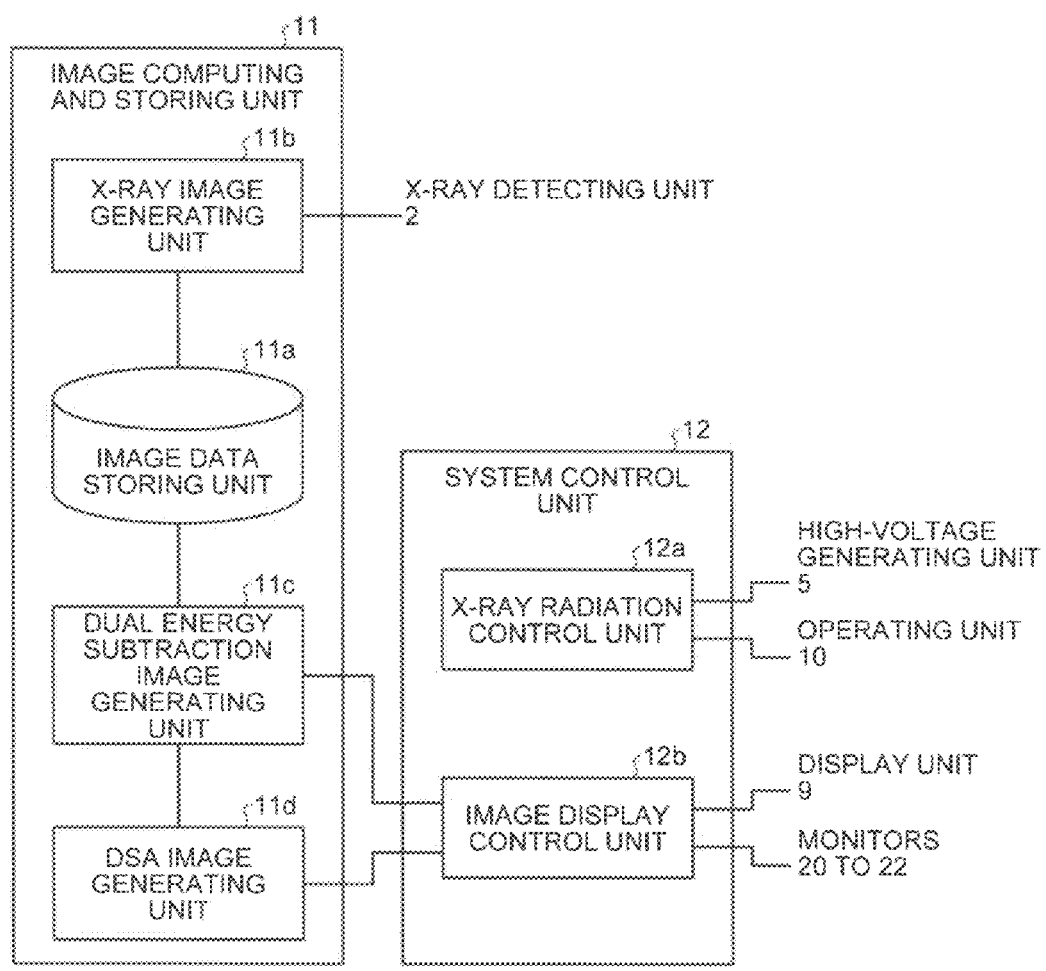
FIG. 2 is a block diagram of functional configurations of an image computing and storing unit and a system control unit.

First, functional configurations of the image computing and storing unit 11 and the system control unit 12 will be explained. FIG. 2 is a block diagram of the functional configurations of the image computing and storing unit 11 and the system control unit 12. As shown in FIG. 2, the image computing and storing unit 11 includes, in particular, an image data storing unit 11a, an X-ray image generating unit 11b, a dual energy subtraction image generating unit 11c, and a DSA image generating unit 11d.

The image data storing unit 11a stores therein X-ray images that have been generated by the X-ray image generating unit 11b. The image data storing unit 11a may be configured with, for example, a Hard Disk Drive (HDD) or a Digital Versatile Disk (DVD) drive.

The X-ray image generating unit 11b generates the X-ray images based on the X-rays that have been detected by the X-ray detecting unit 2. For example, during a dual energy subtraction image taking process, the X-ray image generating unit 11b alternately generates the X-ray images each obtained by radiating the X-rays having the first level of energy and the X-ray images each obtained by radiating the X-rays having the second level of energy that is different from the first level of energy.

The dual energy subtraction image generating unit 11c, every time an X-ray image has been generated by the X-ray image generating unit 11b, generates a dual energy subtraction image by using the X-ray image that has just been generated and the X-ray image generated immediately preceding the X-ray image.

More specifically, when an X-ray image has been generated by the X-ray image generating unit 11b, the dual energy subtraction image generating unit 11c reads the X-ray image generated immediately preceding the generated X-ray image, out of the image data storing unit 11a. Subsequently, the dual energy subtraction image generating unit 11c generates the dual energy subtraction image by applying a predetermined subtraction process to the X-ray image that has just been generated and to the X-ray image generated immediately preceding the X-ray image.

In this situation, by varying a coefficient used in the predetermined subtraction process, the dual energy subtraction image generating unit 11c is also capable of generating an image in which only a particular site is rendered or an image from which a particular site is eliminated.

Figure 3:
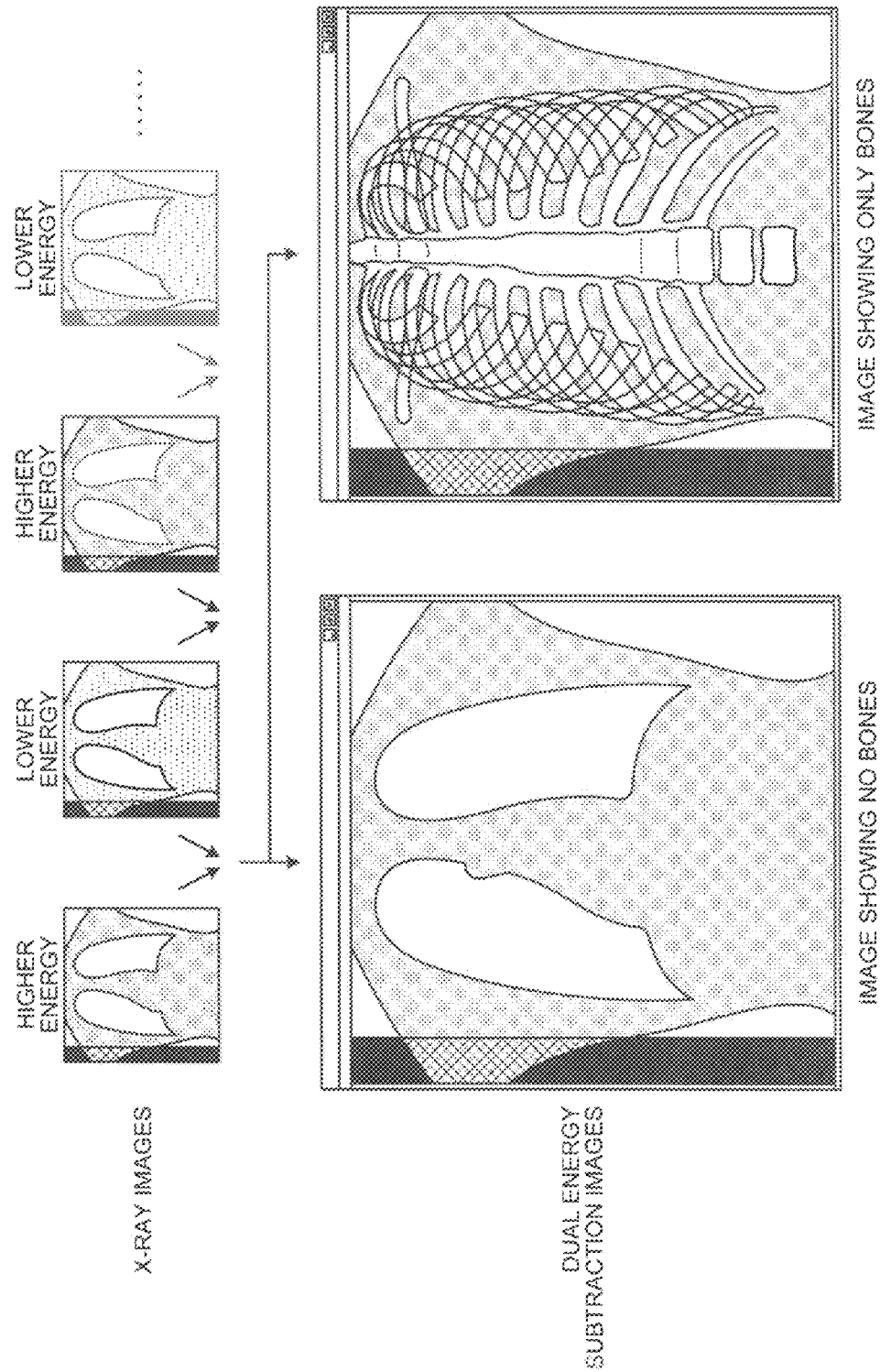
FIG. 3 is a drawing for explaining a dual energy subtraction image generating process performed by a dual energy subtraction image generating unit.

FIG. 3 is a drawing for explaining a dual energy subtraction image generating process performed by the dual energy subtraction image generating unit 11c. As shown in FIG. 3, the dual energy subtraction image generating unit 11c generates, for example, a dual energy subtraction image from which bones are eliminated or in which only bones are rendered, by performing a subtraction process while using an X-ray image obtained by radiating X-rays having a higher level of energy and another X-ray image obtained by radiating X-rays having a lower level of energy. In addition, the dual energy subtraction image generating unit 11c is also capable of generating images in which mutually different sites are rendered, respectively.

The DSA image generating unit 11d generates DSA images by using dual energy subtraction images that are generated before and after a contrast agent is injected to the subject.

Figure 4:
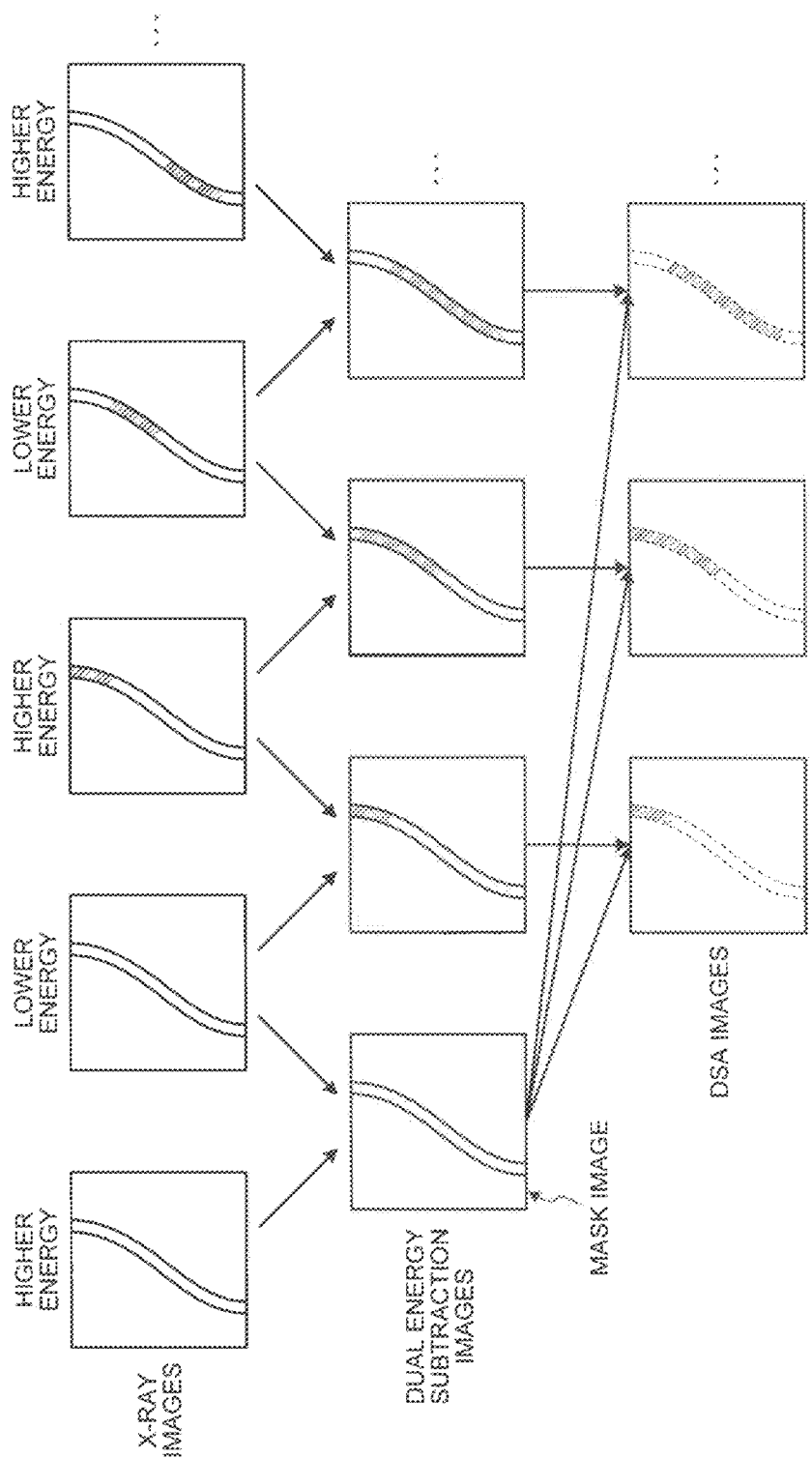
FIG. 4 is a drawing for explaining a DSA image generating process performed by a DSA image generating unit.

FIG. 4 is a drawing for explaining a DSA image generating process performed by the DSA image generating unit 11d. More specifically, as shown in FIG. 4, the DSA image generating unit 11d defines the dual energy subtraction image generated before the contrast agent is injected as a mask image. Further, every time a dual energy subtraction image has been generated by the dual energy subtraction image generating unit 11c by using an X-ray image obtained by radiating the X-rays having the higher level of energy and another X-ray image obtained by radiating the X-rays having the lower level of energy, the DSA image generating unit 11d generates a DSA image by applying a predetermined subtraction process to the generated image and the mask image.

Returning to the description of FIG. 2, the system control unit 12 includes, in particular, an X-ray radiation control unit 12a and an image display control unit 12b.

The X-ray radiation control unit 12a controls the X-ray radiating processes, based on various operations performed by the operator. More specifically, when the operator has instructed that a dual energy subtraction image taking process should be performed, the X-ray radiation control unit 12a controls the high-voltage generating unit 5 so that the level of the voltage supplied to the X-ray tube 1 alternates between a first voltage level and a second voltage level that is lower than the first voltage level.

Accordingly, the X-ray tube 1 alternately radiates the X-rays having the higher level of energy and the X-rays having the lower level of energy onto the subject. As a result, the X-ray image generating unit 11b alternately generates the X-ray images each obtained by radiating the X-rays having the higher level of energy and the X-ray images each obtained by radiating the X-rays having the lower level of energy. Further, the dual energy subtraction image generating unit 11c generates the dual energy subtraction images.

In the first embodiment, the example in which the level of energy of the X-rays radiated onto the subject is changed by changing the level of the voltage supplied to the X-ray tube 1. However, another arrangement is acceptable in which, for example, the level of energy of the X-rays is changed by changing the level of the electric current in the X-ray tube.

The image display control unit 12b displays the various images that have been generated by the dual energy subtraction image generating unit 11c and the DSA image generating unit 11d on the display unit and the monitors 20 to 22.

More specifically, when the dual energy subtraction image generating unit 11c has generated dual energy subtraction images in which mutually different sites are rendered, respectively, the image display control unit 12b displays the dual energy subtraction images on mutually different monitors, respectively, in correspondence with the mutually different sites.

For example, when images of the chest of the subject P have been taken, the image display control unit 12b displays a dual energy subtraction image in which only the bones are rendered on the monitor 20 and displays another dual energy subtraction image in which only the heart is rendered on the monitor 21.

Alternatively, another arrangement is acceptable in which the image display control unit 12b displays the X-ray images that have been generated by the X-ray image generating unit 11b and the dual energy subtraction image that has been generated by the dual energy subtraction image generating unit 11c on mutually different monitors.

In that situation, for example, the image display control unit 12b displays the X-ray image that has been obtained by radiating the X-rays having the higher level of energy on the monitor 20 and displays the X-ray image that has been obtained by radiating the X-rays having the lower level of energy on the monitor 21. Further, the image display control unit 12b displays the dual energy subtraction image that has been generated by the dual energy subtraction image generating unit 11c on the monitor 22.

Alternatively, yet another arrangement is acceptable in which the image display control unit 12b displays the images that have consecutively been generated by the dual energy subtraction image generating unit 11c and the DSA image generating unit 11d as moving pictures on the display unit 9 and on the monitors 20 to 22, respectively.

Figure 5:
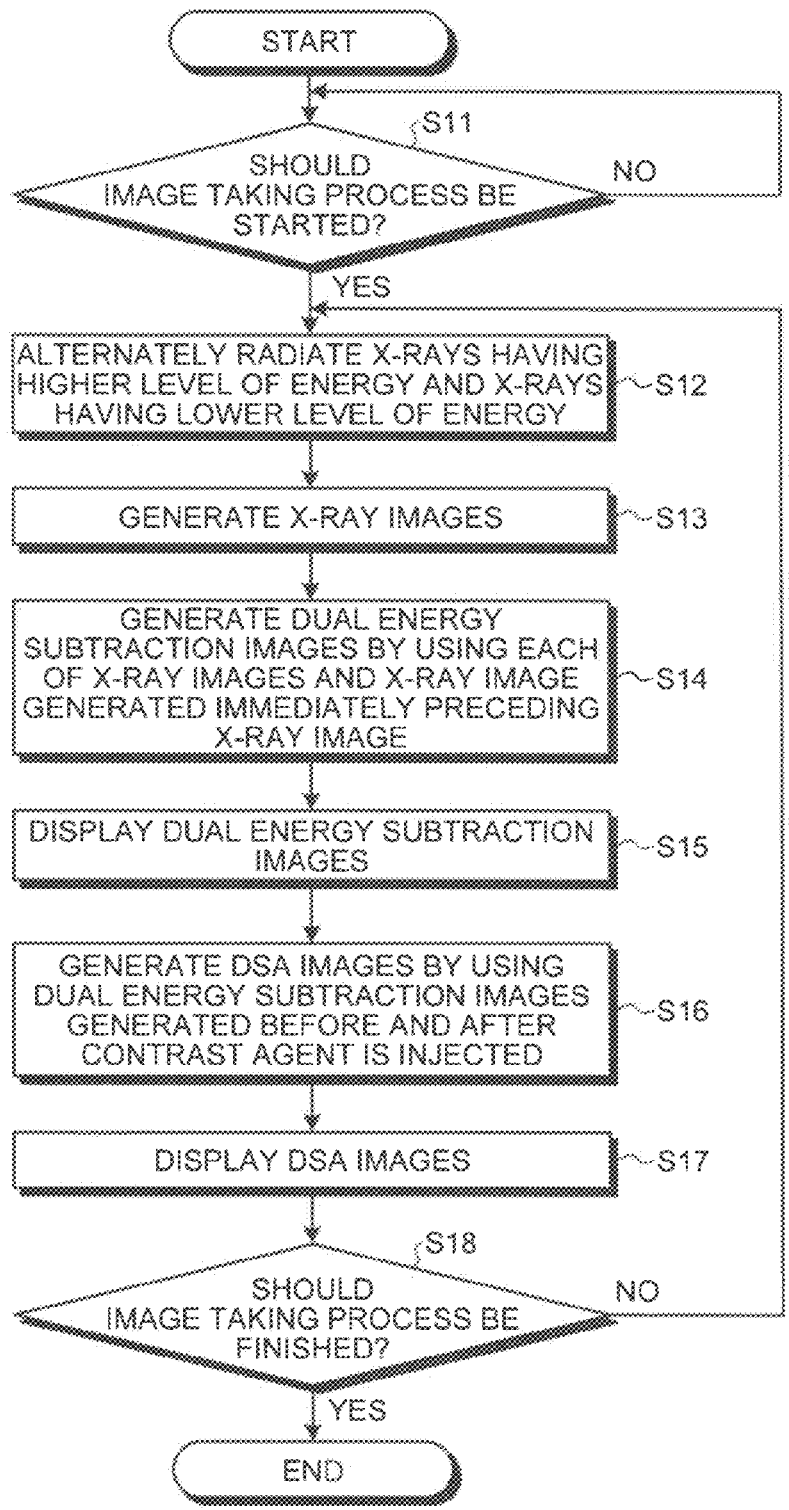
FIG. 5 is a flowchart of a processing procedure in a process performed by the X-ray diagnostic apparatus according to the first embodiment.

Next, a processing procedure in a process performed by the X-ray diagnostic apparatus 100 according to the first embodiment will be explained. FIG. 5 is a flowchart of the processing procedure in the process performed by the X-ray diagnostic apparatus 100 according to the first embodiment. As shown in FIG. 5, while the X-ray diagnostic apparatus 100 according to the first embodiment is being used, when an operator has instructed that an image taking process should be started (step S11: Yes), the X-ray tube 1 alternately radiates X-rays having a higher level of energy and X-rays having a lower level of energy, under the control of the X-ray radiation control unit 12a (step S12).

Subsequently, the X-ray image generating unit 11b generates X-ray images based on the X-rays that have been detected by the X-ray detecting unit 2 (step S13). In this situation, the X-ray image generating unit 11b alternately generates X-ray images each obtained by radiating the X-rays having the higher level of energy and X-ray images each obtained by radiating the X-rays having the lower level of energy.

Further, when each of the X-ray images has been generated by the X-ray image generating unit 11b, the dual energy subtraction image generating unit 11c generates a dual energy subtraction image by using each of the X-ray images that has just been generated and the X-ray image generated immediately preceding the X-ray image (step S14). Subsequently, the image display control unit 12b displays each of the dual energy subtraction images that have been generated by the dual energy subtraction image generating unit 11c on the display unit 9 or any of the monitors 20 to 22 (step S15).

Further, when the dual energy subtraction images have been generated by the dual energy subtraction image generating unit 11c, the DSA image generating unit 11d generates DSA images by using the dual energy subtraction images that have been generated before and after a contract agent is injected to the subject (step S16). After that, the image display control unit 12b displays each of the DSA images that have been generated by the DSA image generating unit 11d on the display unit 9 or any of the monitors 20 to (step S17).

Until the operator instructs that the image taking process should be ended, the X-ray diagnostic apparatus 100 repeatedly performs the process at steps S12 through S17 in the manner described above (step S18: No).

As explained above, according to the first embodiment, the X-ray image generating unit 11b generates the X-ray images each obtained by radiating the X-rays having the higher level of energy and the X-ray images each obtained by radiating the X-rays having the lower level of energy. In addition, every time an X-ray image has been generated by the X-ray image generating unit 11b, the dual energy subtraction image generating unit 11c generates a dual energy subtraction image by using the X-ray image that has just been generated and the X-ray image generated immediately preceding the X-ray image.

With this arrangement, according to the first embodiment, when each of the subtraction processes in the dual energy subtraction process is expressed as $F(2m)-F(2m-1)$ (where m is a natural number), the dual energy subtraction images are generated in the following order: {F(2)−F(1)}, −{F(3)−F(2)}, {F(4)−F(3)}, −{F(5)−F(4)}, {F(6)−F(5)}, and so on. In other words, according to the first embodiment, it is possible to generate as many dual energy subtraction images as the number of times the X-rays are radiated.

With this arrangement, according to the first embodiment, it is possible to generate the subtraction images by performing the dual energy subtraction process more efficiently in relation to the number of times the X-rays are radiated than in the example of the conventional dual energy subtraction process.

Further, in the conventional DSA image taking process, if the subject moves during an image taking process, the image taking process has to be started over again. In contract, in the image taking process according to the first embodiment, the subtraction images are generated from the X-ray images that have been taken consecutively. Accordingly, blurring of the images caused by the moving of the subject decreases. As a result, because the number of times the image taking process has to be started over again decreases, it is possible to reduce the radiation exposure amount of the subject.

Further, according to the first embodiment, the DSA image generating unit 11*d* generates the DSA images by using the dual energy subtraction images that are generated by the dual energy subtraction image generating unit 11*c* before and after the contrast agent is injected to the subject. Thus, according to the first embodiment, it is possible to efficiently perform a diagnosing process or a treatment process on the blood vessels while looking at a DSA image from which the sites other than the blood vessels are eliminated or a DSA image in which the contrast agent or a stent is highlighted.

Furthermore, according to the first embodiment, the dual energy subtraction image generating unit 11*c* generates at least a dual energy subtraction image in which a first site is rendered and another dual energy subtraction image in which a second site that is different from the first site is rendered. Also, the image display control unit 12*b* displays the dual energy subtraction image in which the first site is rendered and said another dual energy subtraction image in which the second site is rendered. With this arrangement, according to the first embodiment, it is possible to efficiently perform a diagnosing process while looking at conditions of the mutually different sites that are displayed side by side.

In addition, according to the first embodiment, the image display control unit 12*b* displays the X-ray images each obtained by radiating the X-rays having the higher level of energy and the X-ray images each obtained by radiating the X-rays having the lower level of energy, as well as the dual energy subtraction images. Thus, according to the first embodiment, it is possible to efficiently perform a diagnosing process while comparing the images that are obtained before and after the subtraction process is performed.

Furthermore, although the X-ray diagnostic apparatus has been explained in the description of the first embodiment, the present invention is not limited to this example. It is possible to apply the present invention likewise to other radiation diagnostic apparatuses that use other radiation rays such as α-rays, β-rays, or γ-rays.

The radiation diagnostic apparatuses mentioned above also include X-ray computed tomography apparatuses. Thus, an example in which the present invention is applied to an X-ray computed tomography apparatus will be explained as a second embodiment of the present invention. In the description of the second embodiment, the X-ray computed tomography apparatus will be referred to as an "X-ray CT apparatus". Also, images generated by the X-ray CT apparatus will be referred to as "CT images".

Figure 6:
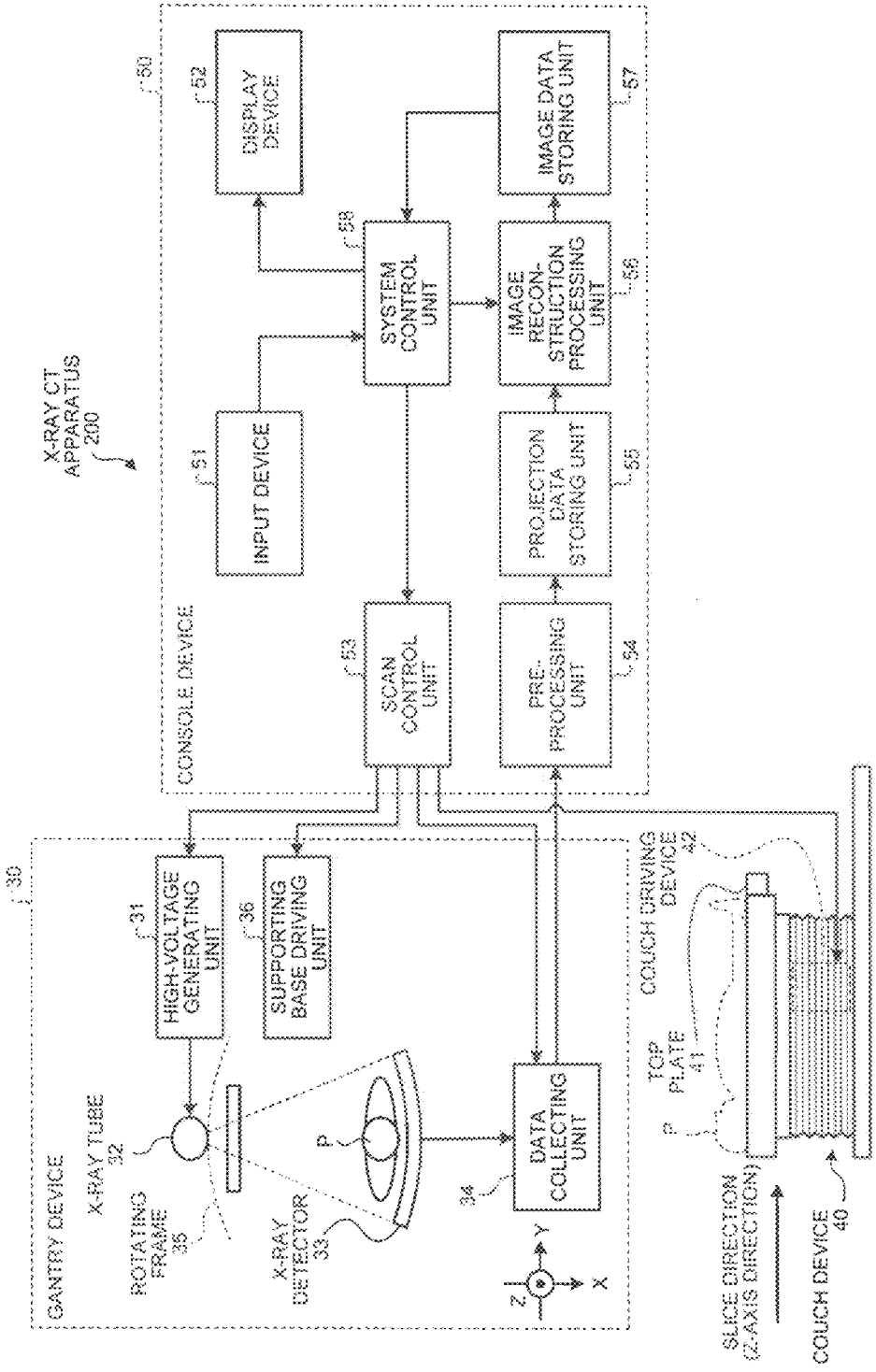
FIG. 6 is a block diagram of an X-ray CT apparatus according to a second embodiment of the present invention.

First, a configuration of the X-ray CT apparatus according to the second embodiment will be explained. FIG. 6 is a block diagram of an X-ray CT apparatus 200 according to the second embodiment. As shown in FIG. 6, the X-ray CT apparatus 200 includes a gantry device 30, a couch device 40, and a console device 50.

The gantry device 30 is a device that radiates X-rays onto the subject P and collects projection data. The gantry device 30 includes a high-voltage generating unit 31, an X-ray tube 32, an X-ray detector 33, a data collecting unit 34, a rotating frame 35, and a gantry driving unit 36.

The high-voltage generating unit 31 supplies a high voltage to the X-ray tube 32. The X-ray tube 32 generates X-rays by using the high voltage supplied by the high-voltage generating unit 31.

The X-ray detector 33 detects X-ray intensity distribution data indicating an intensity distribution of the X-rays that have passed through the subject P. The X-ray detector 33 may be configured with, for example, a multi-detector-row area detector obtained by arranging a plurality of detecting element rows (e.g., 320 rows) in a slice direction (i.e., the Z-axis direction shown in FIG. 6), the detecting element rows each being made up of X-ray detecting elements corresponding to a plurality of channels.

The data collecting unit 34 generates the projection data from the X-ray intensity distribution data that has been detected by the X-ray detector 33. For example, the data collecting unit 34 generates two-dimensional projection data by performing an amplifying process or an Analog/Digital (A/D) conversion process on the X-ray intensity distribution data. Also, the data collecting unit 34 sends the generated projection data to the console device 50.

The rotating frame 35 is configured so as to have an annular shape and to rotate continuously at a high speed. The rotating frame 35 supports the X-ray tube 32 and the X-ray detector 33 in such a manner that the X-ray tube 32 and the X-ray detector 33 oppose each other while the subject P is interposed therebetween. The gantry driving unit 36 causes the X-ray tube 32 and the X-ray detector 33 to revolve on a circular orbit that is centered on the subject P, by rotating and driving the rotating frame 35.

The couch device 40 is a device on which the subject P can be placed and includes a top plate 41 and a couch driving device 42. The top plate 41 is a plate on which the subject P is placed while an image taking process is performed. The couch driving device 42 is a device that moves the top plate 41 in the slice direction.

The console device 50 receives various instructions related to operations of the X-ray CT apparatus 200 from the operator and reconstructs an image from the projection data that has been collected by the gantry device 30. The console device 50 includes an input device 51, a display device 52, a scan control unit 53, a pre-processing unit 54, a projection data storing unit 55, an image reconstruction processing unit 56, an image data storing unit 57, and a system control unit 58.

The input device 51 includes a mouse and/or a keyboard and receives instructions to the X-ray CT apparatus 200 from the operator. For example, the input device 51 receives, from the operator, inputs of conditions under which an image taking process is to be performed, such as the intervals at which the X-rays are radiated, the time period during which the image taking process is performed, and the level of the tube electric current supplied to the X-ray tube.

The display device 52 includes a display device such as a Liquid Crystal Display (LCD) device and displays various types of information. For example, the display device 52 displays image data stored in the image data storing unit 57 (explained later) and a Graphical User Interface (GUI) used for receiving various instructions from the operator.

Under the control of the system control unit 58 (explained later), the scan control unit 53 drives the high-voltage generating unit 31, the data collecting unit 34, the gantry driving unit 36, and the couch driving device 42, based on the image-taking conditions that have been set by the operator. When the scan control unit 53 drives these elements, the projection data related to the subject P is collected.

The pre-processing unit 54 performs a pre-processing process such as a sensitivity correction process on the projection data that has been generated by the data collecting unit 34. Also, the pre-processing unit 54 stores the projection data on which the pre-processing process has been performed into the projection data storing unit 55.

The projection data storing unit 55 stores therein the projection data on which the pre-processing process has been performed by the pre-processing unit 54. The projection data storing unit 55 may be configured with, for example, a hard disk device or an optical disk device.

Under the control of the system control unit 58 (explained later), the image reconstruction processing unit 56 reads the projection data stored in the projection data storing unit 55 and reconstructs CT images by performing a back projection process on the projection data that has been read. Also, the image reconstruction processing unit 56 stores the reconstructed CT images into the image data storing unit 57.

The image data storing unit 57 stores therein the CT images that have been reconstructed by the image reconstruction processing unit 56. The image data storing unit 57 may be configured with, for example, a hard disk device or an optical disk device.

The system control unit 58 exercises overall control of the X-ray CT apparatus 200 by controlling operations of the gantry device 30, the couch device 40, and the console device 50. For example, the system control unit 58 has the projection data collected and has the CT images reconstructed by controlling the operations of the gantry device 30, the couch device 40, and the console device 50, based on the image-taking conditions that have been received from the operator via the input device 51.

The configuration of the X-ray CT apparatus 200 according to the second embodiment has thus been explained. In the X-ray CT apparatus 200 according to the second embodiment that is configured as described above, the X-ray tube 32 alternately radiates X-rays having a first level of energy and X-rays having a second level of energy that is different from the first level of energy onto the subject P. Also, the image reconstruction processing unit 56 generates a first CT image based on the X-rays that have been detected by the X-ray detector 33 when the X-rays having the first level of energy were radiated and generates a second CT image based on the X-rays that have been detected by the X-ray detector 33 when the X-rays having the second level of energy were radiated. Further, every time a first CT image or a second CT image has been generated, the image reconstruction processing unit 56 generates a subtraction image by using the first CT image or the second CT image that has just been generated and the CT image generated immediately preceding the first CT image or the second CT image. As a result, according to the second embodiment, it is possible to efficiently generate the subtraction images by performing the dual energy subtraction process. In the following sections, functions of the X-ray CT apparatus 200 that is configured as described above will be explained in detail.

Figure 7:
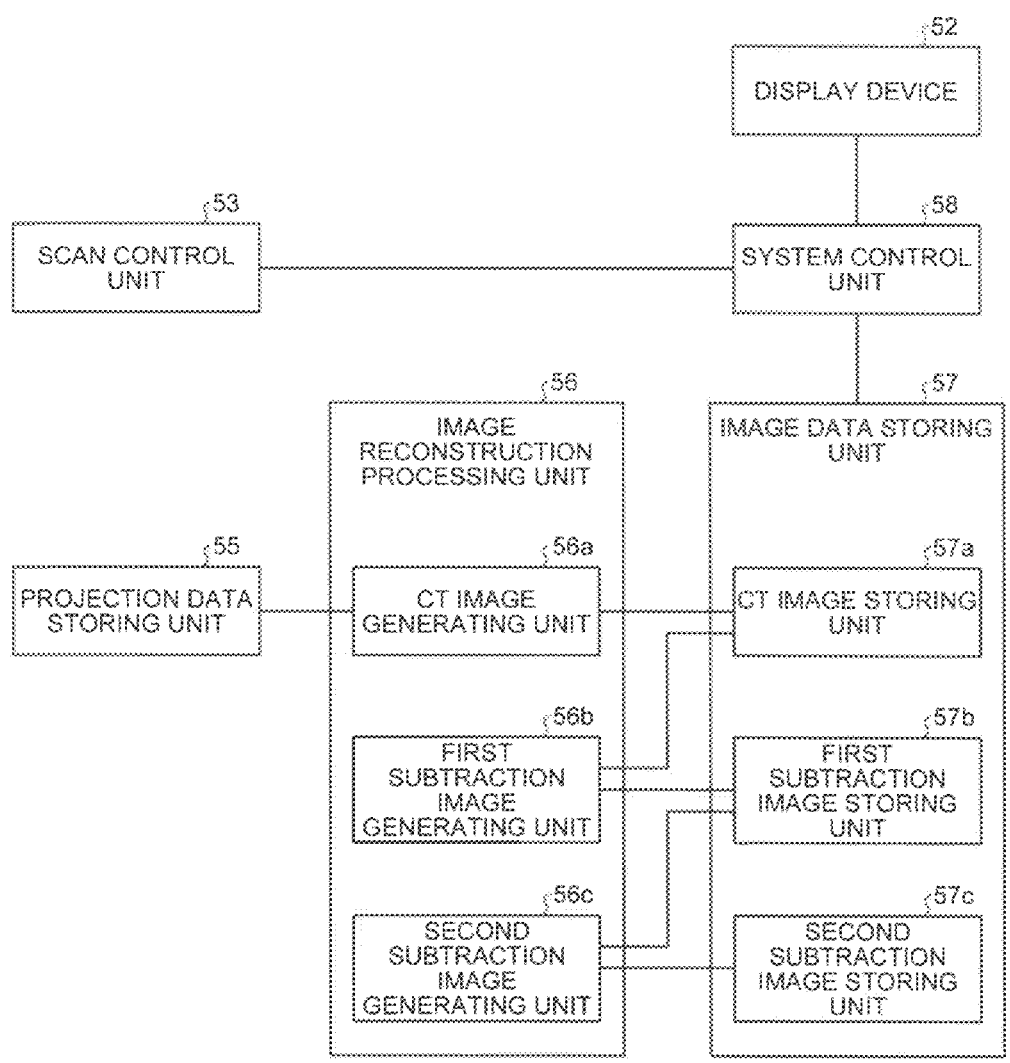
FIG. 7 is a functional block diagram of detailed configurations of the X-ray CT apparatus according to the second embodiment.

FIG. 7 is a functional block diagram of detailed configurations of the X-ray CT apparatus 200 according to the second embodiment. Of the constituent elements shown in FIG. 6, the display device 52, the scan control unit 53, the projection data storing unit 55, the image reconstruction processing unit 56, and the image data storing unit 57 are shown in FIG. 7.

According to the second embodiment, the system control unit 58 controls the X-ray tube 32 in such a manner that, in correspondence with every rotation of the rotating frames 35, the X-ray tube 32 alternately radiates the X-rays having the first level of energy and the X-rays having the second level of energy that is different from the first level of energy onto the subject P. In the present example, it is assumed that the first level of energy is higher than the second level of energy.

Further, as shown in FIG. 7, the image data storing unit 57 includes a CT image storing unit 57a, a first subtraction image storing unit 57b, and a second subtraction image storing unit 57c.

The CT image storing unit 57a stores therein CT images that have been generated by a CT image generating unit 56a (explained later). The first subtraction image storing unit 57b stores therein subtraction images that have been generated by a first subtraction image generating unit 56b (explained later). The second subtraction image storing unit 57c stores therein subtraction images that have been generated by a second subtraction image generating unit 56c (explained later).

Also, as shown in FIG. 7, the image reconstruction processing unit 56 includes the CT image generating unit 56a, the first subtraction image generating unit 56b, and the second subtraction image generating unit 56c.

The CT image generating unit 56a generates the first CT image based on the X-rays that have been detected by the X-ray detector 33 when the X-rays having the higher level of energy were radiated and generates the second CT image based on the X-rays that have been detected by the X-ray detector 33 when the X-rays having the lower level of energy were radiated. Subsequently, the CT image generating unit 56a stores the CT images that have been generated into the CT image storing unit 57a.

Every time a first CT image or a second CT image has been generated by the CT image generating unit 56a, the first subtraction image generating unit 56b generates a first subtraction image by using the first CT image or the second CT image that has just been generated and the CT image generated immediately preceding the first CT image or the second CT image. The first subtraction image generated in this situation is, for example, an image in which only a particular site is rendered.

More specifically, when a first CT image has been generated by the CT image generating unit 56a, the first subtraction image generating unit 56b reads the generated first CT image and the second CT image generated immediately preceding the first CT image, out of the CT image storing unit 57a. Subsequently, the first subtraction image generating unit 56b generates a first subtraction image by calculating a difference between the first CT image and the second CT image that have been read.

Also, when a second CT image has been generated by the CT image generating unit 56a, the first subtraction image generating unit 56b reads the generated second CT image and the first CT image generated immediately preceding the second CT image, out of the CT image storing unit 57*a*. Subsequently, the first subtraction image generating unit 56*b* generates another first subtraction image by calculating a difference between the second CT image and the first CT image that have been read.

After that, the first subtraction image generating unit 56*b* stores the first subtraction images that have been generated into the first subtraction image storing unit 57*b*.

The second subtraction image generating unit 56*c* generates second subtraction images by using the first subtraction images that have been generated by the first subtraction image generating unit 56*b* before and after a contrast agent is injected to the subject P. The second subtraction images generated in this situation are images from which the sites other than the blood vessels are eliminated.

Further, according to the second embodiment, the system control unit 58 displays the subtraction images that have been generated by the first subtraction image generating unit 56*b* and the second subtraction image generating unit 56*c* on the display device 52.

For example, the system control unit 58 displays a first subtraction image that has been generated by the first subtraction image generating unit 56*b* and a second subtraction image that has been generate by the second subtraction image generating unit 56*c* that are arranged in a row on the display device 52. In this situation, another arrangement is acceptable in which the system control unit 58 displays the subtraction images that have consecutively been generated by the first subtraction image generating unit 56*b* and by the second subtraction image generating unit 56*c* on the display device 52 as moving pictures.

Figure 8:
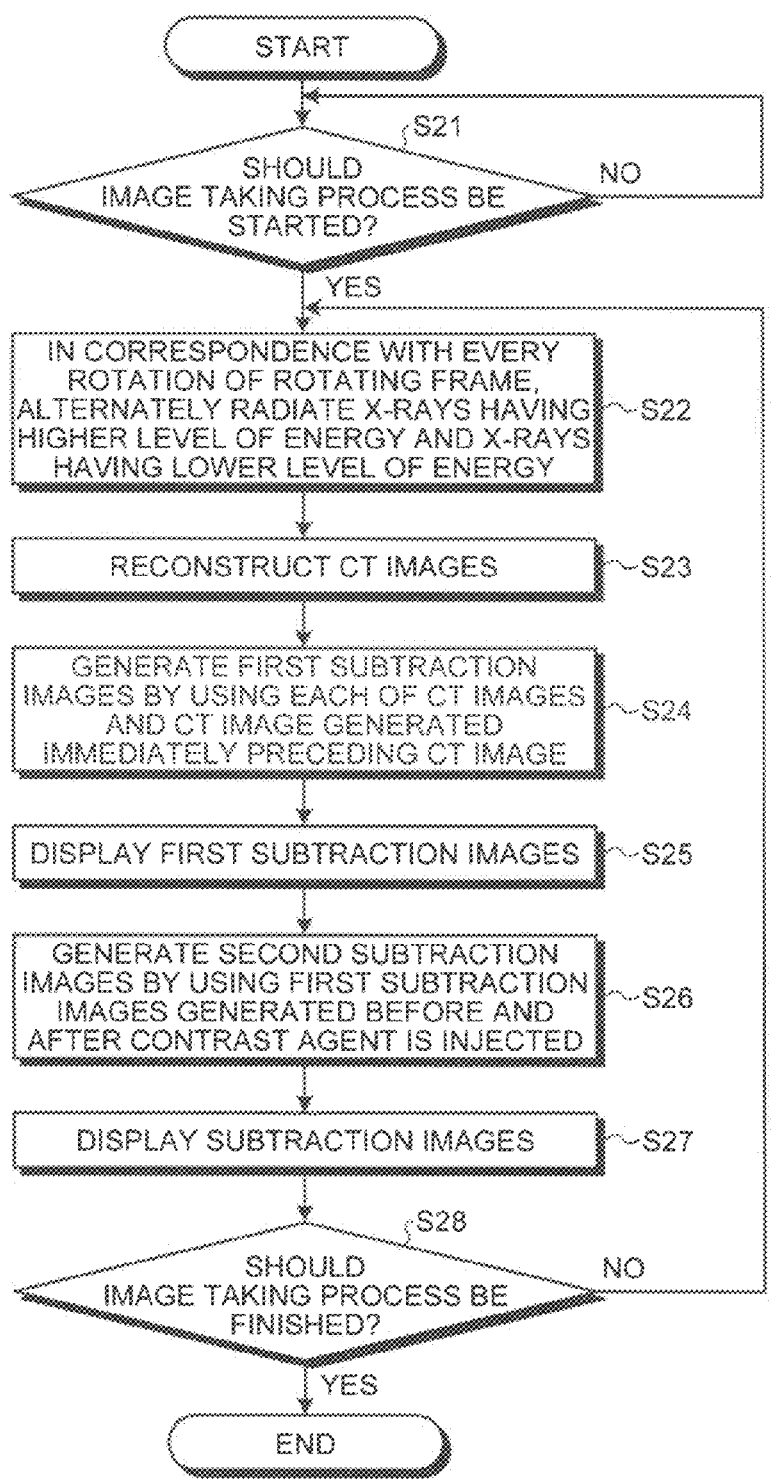
FIG. 8 is a flowchart of a processing procedure in a process performed by the X-ray CT apparatus according to the second embodiment.

Next, a processing procedure in a process performed by the X-ray CT apparatus 200 according to the second embodiment will be explained. FIG. 8 is a flowchart of the processing procedure in the process performed by the X-ray CT apparatus 200 according to the second embodiment.

As shown in FIG. 8, while the X-ray CT apparatus 200 is being used, when an operator has instructed that an image taking process should be started (step S21: Yes), in correspondence with every rotation of the rotating frame 35, the X-ray tube 32 alternately radiates X-rays having a higher level of energy and X-rays having a lower level of energy, under the control of the system control unit 58 (step S22).

Subsequently, the CT image generating unit 56*a* generates first CT images based on the X-rays that have been detected by the X-ray detector 33 when the X-rays having the higher level of energy were radiated and generates second CT images based on the X-rays that have been detected by the X-ray detector 33 when the X-rays having the lower level of energy were radiated (step S23).

Further, every time a first CT image or a second CT image has been generated by the CT image generating unit 56*a*, the first subtraction image generating unit 56*b* generates a first subtraction image by using the first CT image or the second CT image that has just been generated and the CT image generated immediately preceding the first CT image or the second CT image (step S24). Subsequently, the system control unit 58 displays the first subtraction images that have been generated by the first subtraction image generating unit 56*b* on the display device 52 (step S25).

After that, the second subtraction image generating unit 56*c* generates second subtraction images by using the first subtraction images that have been generated by the first subtraction image generating unit 56*b* before and after a contrast agent is injected to the subject (step S26). Subsequently, the system control unit 58 displays the subtraction images that have been generated by the first subtraction image generating unit 56*b* and the second subtraction image generating unit 56*c* on the display device 52 (step S27).

Until the operator instructs that the image taking process should be ended, the X-ray CT apparatus 200 repeatedly performs the process at steps S22 through S27 in the manner described above (step S28: No).

As explained above, according to the second embodiment, the X-ray tube 32 alternately radiates the X-rays having the first level of energy and the X-rays having the second level of energy that is different from the first level of energy onto the subject P. In addition, the CT image generating unit 56*a* generates the first CT images based on the X-rays that have been detected by the X-ray detector 33 when the X-rays having the first level of energy were radiated and generates the second CT images based on the X-rays that have been detected by the X-ray detector 33 when the X-rays having the second level of energy were radiated. Further, every time a first CT image or a second CT image has been generated, the first subtraction image generating unit 56*b* generates a subtraction image by using the first CT image or the second CT image that has just been generated and the CT image generated immediately preceding the first CT image or the second CT image. With this arrangement, according to the second embodiment, by using the X-ray CT apparatus 200, it is possible to efficiently generate the subtraction images by performing the dual energy subtraction process.

Further, according to the second embodiment, the second subtraction image generating unit 56*c* generates the second subtraction images by using the first subtraction images that have been generated by the first subtraction image generating unit 56*b* before and after the contrast agent is injected to the subject. With this arrangement, according to the second embodiment, by using the X-ray CT apparatus 200, it is possible to efficiently perform a diagnosing process or a treatment process on the blood vessels while looking at the subtraction images.

In the description of the second embodiment above, the example in which, in correspondence with every rotation of the rotating frame, the X-rays having the first level of energy and the X-rays having the second level of energy are radiated alternately. However, the present invention is not limited to this example.

X-ray CT apparatuses are configured so as to radiate X-rays onto a subject from mutually different projection directions by revolving an X-ray tube and an X-ray detector that are disposed so as to oppose each other while the subject is interposed therebetween, in such a manner that the revolution is centered on the subject. In this situation, the projection directions that are used as X-ray radiating units will be referred to as "views". X-ray CT apparatuses are further configured so as to generate a piece of projection data for each of the views.

Accordingly, an arrangement is acceptable in which, for example, the level of energy of the X-ray is changed so as to alternate in correspondence with each of the views, so that it is possible to generate pieces of difference data for the pieces of projection data that are respectively generated in correspondence with the views. In the following sections, such an arrangement will be explained as a third embodiment of the present invention.

Figure 9:
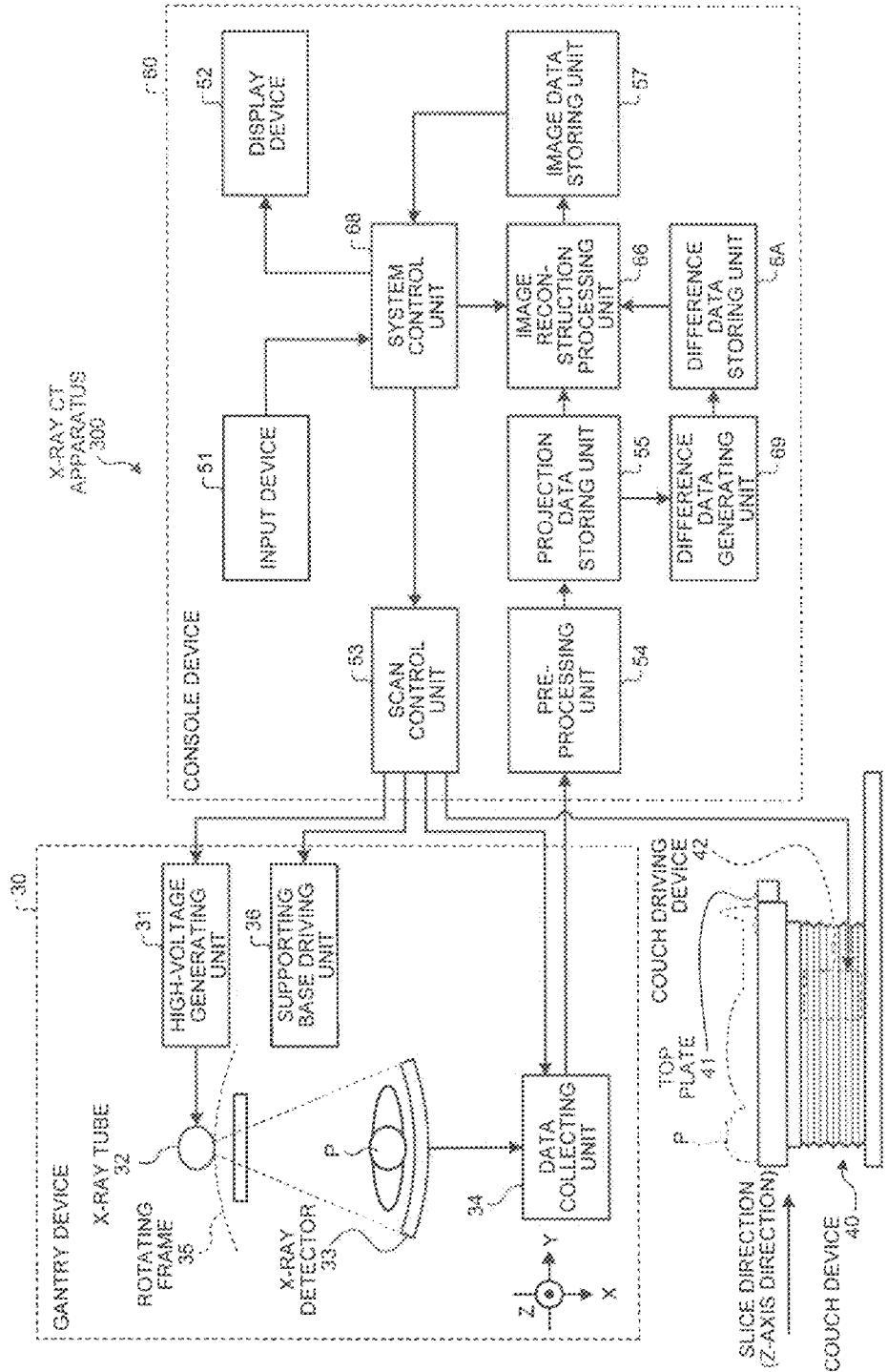
FIG. 9 is a block diagram of an X-ray CT apparatus according to a third embodiment of the present invention.

First, a configuration of an X-ray CT apparatus according to the third embodiment will be explained. FIG. 9 is a block diagram of an X-ray CT apparatus 300 according to the third embodiment. In the following sections, for the sake of convenience in explanation, some of the functional elements that assume the same roles as those shown in FIG. 6 will be referred to by using the same reference characters, and the explanation thereof will be omitted.

As shown in FIG. 9, the X-ray CT apparatus 300 includes the gantry device 30, the couch device 40, and a console device 60.

The console device 60 is a device that receives various instructions related to operations of the X-ray CT apparatus 300 from the operator and reconstructs an image from the projection data that has been collected by the gantry device 30. The console device 60 includes the input device 51, the display device 52, the scan control unit 53, the pre-processing unit 54, the projection data storing unit 55, an image reconstruction processing unit 66, the image data storing unit 57, a system control unit 68, and a difference data storing unit 6A.

According to the third embodiment, the system control unit 68 controls the X-ray tube 32 in such a manner that, in correspondence with each of the views, the X-ray tube 32 alternately radiates X-rays having a first level of energy and X-rays having a second level of energy that is different from the first level of energy onto the subject P. In the present example, it is assumed that the first level of energy is higher than the second level of energy.

In this situation, the data collecting unit 34 generates pieces of first projection data based on the X-rays that have been detected by the X-ray detector 33 when the X-rays having the higher level of energy were radiated and generates pieces of second projection data based on the X-rays that have been detected by the X-ray detector 33 when the X-rays having the lower level of energy were radiated. As a result, the projection data storing unit 55 alternately stores therein the pieces of first projection data and the pieces of second projection data, in correspondence with each of the views.

Further, every time a piece of first projection data or a piece of second projection data has been generated by the data collecting unit 34, a difference data generating unit 69 generates a piece of difference data corresponding to the difference between the piece of first projection data or the piece of second projection data that has just been generated and the piece of projection data generated immediately preceding the piece of first projection data or the piece of second projection data.

More specifically, the difference data generating unit 69 reads the pieces of first projection data and the pieces of second projection data that have alternately been generated by the data collecting unit 34 out of the projection data storing unit 55, in the order the pieces of projection data were generated. Further, every time a piece of projection data has been read, the difference data generating unit 69 generates a piece of difference data corresponding to the difference between the piece of projection data that has just been read and the piece of projection data read immediately preceding the piece of projection data.

After that, the difference data generating unit 69 stores the pieces of difference data that have been generated into the difference data storing unit 6A. The difference data storing unit 6A stores therein the pieces of difference data that have been generated by the difference data generating unit 69.

The image reconstruction processing unit 66 reconstructs CT images from the pieces of projection data that are stored in the projection data storing unit 55 in the same manner as described in the second embodiment. In addition, according to the third embodiment, the image reconstruction processing unit 66 also reconstructs CT images from the pieces of difference data that are stored in the difference data storing unit 6A.

More specifically, the image reconstruction processing unit 66 reads the pieces of difference data that are stored in the difference data storing unit 6A and reconstructs the CT images by performing a back projection process on the read pieces of difference data. Each of the CT images that are generated in this situation may be a two-dimensional image or a three-dimensional image. After that, the image reconstruction processing unit 66 stores the CT images that have been reconstructed into the image data storing unit 57.

Further, according to the third embodiment, the system control unit 68 displays the CT images that have been generated by the image reconstruction processing unit 66 on the display device 52. In this situation, another arrangement is acceptable in which the system control unit 68 displays the CT images that have consecutively been generated by the image reconstruction processing unit 66 on the display device 52 as a moving picture.

Figure 10:
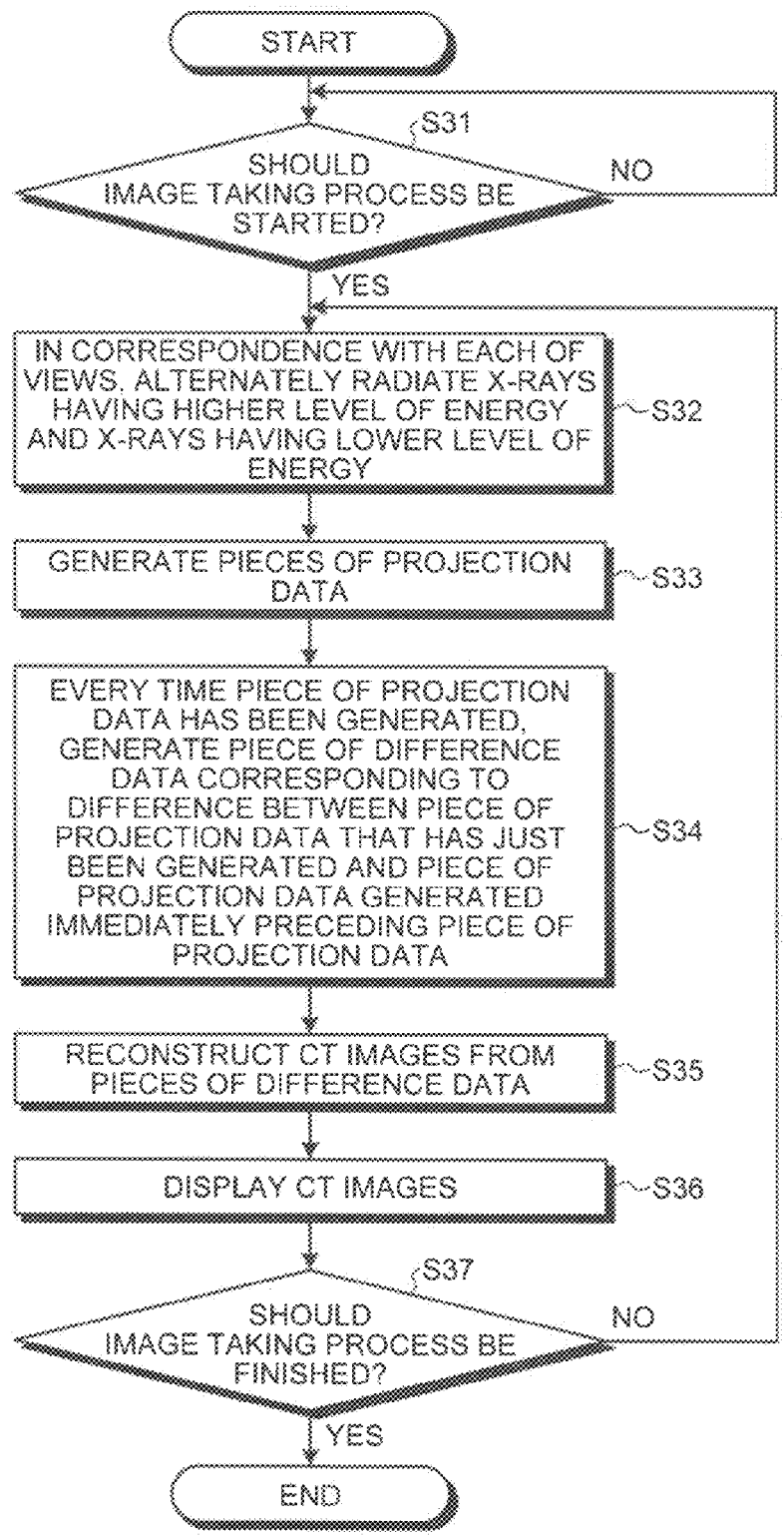
FIG. 10 is a flowchart of a processing procedure in a process performed by the X-ray CT apparatus according to the third embodiment.

Next, a processing procedure in a process performed by the X-ray CT apparatus 300 according to the third embodiment will be explained. FIG. 10 is a flowchart of the processing procedure in the process performed by the X-ray CT apparatus 300 according to the third embodiment.

As shown in FIG. 10, while the X-ray CT apparatus 300 is being used, when an operator has instructed that an image taking process should be started (step S31: Yes), in correspondence with each of the views, X-rays having a higher level of energy and X-rays having a lower level of energy are alternately radiated onto the subject P, under the control of the system control unit 68 (step S32).

Subsequently, the data collecting unit 34 generates pieces of first projection data based on the X-rays that have been detected by the X-ray detector 33 when the X-rays having the higher level of energy were radiated and generates pieces of second projection data based on the X-rays that have been detected by the X-ray detector 33 when the X-rays having the lower level of energy were radiated (step S33).

Further, every time a piece of first projection data or a piece of second projection data has been generated by the data collecting unit 34, the difference data generating unit 69 generates a piece of difference data corresponding to the difference between the piece of first projection data or the piece of second projection data that has just been generated and the piece of projection data generated immediately preceding the piece of first projection data or the piece of second projection data (step S34).

Subsequently, the image reconstruction processing unit 66 reconstructs CT images from the pieces of difference data that have been generated by the difference data generating unit 69 (step S35). Subsequently, the system control unit 68 displays the CT images that have been generated by the image reconstruction processing unit 66 on the display device 52 (step S36).

Until the operator instructs that the image taking process should be ended, the X-ray CT apparatus 300 repeatedly performs the process at steps S32 through S36 in the manner described above (step S37: No).

As explained above, according to the third embodiment, the X-ray tube 32 alternately radiates the X-rays having the first level of energy and the X-rays having the second level of energy that is different from the first level of energy onto the subject from the mutually different projection directions. In addition, the data collecting unit 34 generates the pieces of first projection data based on the X-rays that have been detected by the X-ray detector 33 when the X-rays having the first level of energy were radiated and generates the pieces of second projection data based on the X-rays that have been detected by the X-ray detector 33 when the X-rays having the second level of energy were radiated. Further, every time a piece of first projection data or a piece of second projection data has been generated by the data collecting unit 34, the difference data generating unit 69 generates a piece of difference data corresponding to the difference between the piece of first projection data or the piece of second projection data that has just been generated and the piece of projection data generated immediately preceding the piece of first projection data or the piece of second projection data. Subsequently, the image reconstruction processing unit 66 reconstructs the images from the pieces of difference data that have been generated by the difference data generating unit 69. With this arrangement, it is possible to collect the projection data in correspondence with the plurality of energy states, without having to cause the X-ray tube 32 to revolve around the subject a plurality of times. Further, it is possible to reconstruct the CT images based on the projection data in correspondence with the plurality of energy states.

As explained above, the radiation diagnostic apparatus, the X-ray computed tomography apparatus, and the image processing method according to an aspect of the present invention is useful when a dual energy subtraction image is generated from X-ray images. In particular, the aspect of the present invention is suitable in a situation where it is demanded that a dual energy subtraction image be generated efficiently in relation to the number of times the X-rays are radiated.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A radiation diagnostic apparatus comprising:
an X-ray tube that alternately radiates radiation rays having a first level of energy and radiation rays having a second level of energy that is different from the first level of energy onto a subject;
an X-ray detector that detects radiation rays that have passed through the subject; and
a processing unit configured to:
alternately generate, at a first frame rate, an image based on the radiation rays that have been detected by the X-ray detector when the radiation rays having the first level of energy were radiated and an image based on the radiation rays that have been detected by the X-ray detector when the radiation rays having the second level of energy were radiated; and
successively generate a plurality of subtraction images in which a first site is rendered at a second frame rate higher than the first frame rate, wherein the processing unit generates one of the subtraction images by a first calculation using a first image and a second image generated next to the first image, and subsequently generates one of the subtraction images by a second calculation using the second image and a third image generated next to the second image, wherein the first and third images are the image of the first level of energy, and the second image is the image of the second level of energy.

2. The radiation diagnostic apparatus according to claim 1, wherein
the processing unit generates the plurality of subtraction images as first subtraction images, and
the processing unit further generates a second subtraction image by using the first subtraction images that are generated before and after a contrast agent is injected to the subject.

3. The radiation diagnostic apparatus according to claim 1, wherein
the processing unit generates, as the plurality of subtraction images, at least a subtraction image in which the first site is rendered and another subtraction image in which a second site that is different from the first site is rendered, and
the processing unit further causes a display to display the subtraction image in which the first site is rendered and the another subtraction image in which the second site is rendered.

4. The radiation diagnostic apparatus according to claim 1, wherein the processing unit further causes a display to display the image of the first level of energy and the image of the second level of energy as well as at least one of the subtraction images.

5. The radiation diagnostic apparatus according to claim 1, wherein the processing unit further causes a display to display the subtraction images generated consecutively as a moving picture.

6. The radiation diagnostic apparatus according to claim 1, wherein the first calculation and the second calculation are different calculations.

7. The radiation diagnostic apparatus according to claim 6, wherein
the first calculation is a calculation subtracting, from the first image of the first level of energy, the second image of the second level of energy generated next to the first image, and
the second calculation is a calculation subtracting, from the third image of the second level of energy, the second image of the first level of energy generated next to the first image.

8. The radiation diagnostic apparatus according to claim 1, wherein
the processing unit alternately generates a first pair of the first image and the second image and a second pair of the third image and a fourth image, wherein the first and third images are the image of the first level of energy, and the second and fourth images are the image of the second level of energy,
the first calculation is a calculation using the first image of the first level of energy included in the first pair and the second image of the second level of energy included in the first pair, and
the second calculation is a calculation using the second image of the second level of energy included in the first pair and the third image of the first level of energy included in the second pair generated next to the first pair.

9. An X-ray computed tomography apparatus comprising:
an X-ray tube that alternately radiates X-rays having a first level of energy and X-rays having a second level of energy that is different from the first level of energy onto a subject from mutually different projection directions;
an X-ray detector that detects X-rays that have passed through the subject; and
a processing unit configured to:
alternately generate, at a first sampling rate, a piece of first projection data based on the X-rays that have been detected by the X-ray detector when the X-rays having the first level of energy were radiated and a piece of second projection data based on the X-rays that have been detected by the X-ray detector when the X-rays having the second level of energy were radiated;

successively generate a plurality of pieces of difference data at a second sampling rate higher than the first sampling rate, wherein the processing unit generates one of the pieces of difference data by a first calculation using a piece of first projection data and a piece of second projection data generated next to the piece of first projection data, and subsequently generates one of the piece of difference data by a second calculation using the piece of second projection data and a piece of third projection data generated next to the piece of second data, wherein the pieces of first and third projection data are the piece of projection data of the first level of energy, and the piece of second projection data is the piece of projection data of the second level of energy; and reconstruct an image from the pieces of difference data.

10. The X-ray computed tomography apparatus according to claim 9, wherein the processing unit further causes a display to display the images generated consecutively as a moving picture.

11. The X-ray computed tomography apparatus according to claim 9, wherein the X-ray tube alternately radiates the X-rays having the first level of energy and the X-rays having the second level of energy in correspondence with every rotation of a rotating frame that rotates continuously and supports the X-ray tube and the X-ray detector such that the X-ray tube and the X-ray detector oppose each other while the subject is interposed therebetween.

12. An image processing method comprising:
alternately radiating radiation rays having a first level of energy and radiation rays having a second level of energy that is different from the first level of energy onto a subject;
detecting radiation rays that have passed through the subject;
alternately generating, at a first frame rate, an image based on the radiation rays that have been detected when the radiation rays having the first level of energy were radiated and an image based on the radiation rays that have been detected when the radiation rays having the second level of energy were radiated; and
successively generating a plurality of subtraction images in which a first site is rendered at a second frame rate higher than the first frame rate, wherein one of the subtraction images is generated by a first calculation using a first image and a second image next to the first image, and one of the subtraction images is subsequently generated by a second calculation using the second image and a third image generated next to the second image, wherein the first and third images are the image of the first level of energy, and the second image is the image of the second level of energy.

13. The imaging processing method according to claim 12, further comprising
generating the plurality of subtraction images as first subtraction images, and
generating a second subtraction image by using the first subtraction images that are generated before and after a contrast agent is injected to the subject.

14. The imaging processing method according to claim 12, further comprising generating, as the plurality of subtraction images, at least a subtraction image in which the first site is rendered and another subtraction image in which a second site that is different from the first site is rendered, and
causing a display to display the subtraction image in which the first site is rendered and the another subtraction image in which the second site is rendered.

15. The imaging processing method according to claim 12, further comprising causing a display to display the image of the first level of energy and the image of the second level of energy as well as at least one of the subtraction images.

16. The imaging processing method according to claim 12, further comprising causing a display to display the subtraction images generated consecutively as a moving picture.

17. The imaging processing method according to claim 12, wherein the first calculation and the second calculation are different calculations.

18. The imaging processing method according to claim 17, wherein
the first calculation is a calculation subtracting, from the first image of the first level of energy, the second image of the second level of energy generated next to the first image, and
the second calculation is a calculation subtracting, from the third image of the second level of energy, the second image of the first level of energy generated next to the first image.

19. The imaging processing method according to claim 12, further comprising
alternately generating a first pair of the first image and the second image and a second pair of the third image and a fourth image, wherein the first and third images are the image of the first level of energy, and the second and fourth images are the image of the second level of energy,
the first calculation is a calculation using the first image of the first level of energy included in the first pair and the second image of the second level of energy included in the first pair, and
the second calculation is a calculation using the second image of the second level of energy included in the first pair and the third image of the first level of energy included in the second pair generated next to the first pair.

20. A X-ray computed tomography apparatus comprising:
an X-ray tube that alternately radiates X-rays having a first level of energy and X-rays having a second level of energy that is different from the first level of energy onto a subject from mutually different projection directions;
an X-ray detector that detects X-rays that have passed through the subject; and
a processing unit configured to:
alternately generate, at a first frame rate, an image based on the X-rays that have been detected by the X-ray detector when the X-rays having the first level of energy were radiated and an image based on the X-rays that have been detected by the X-ray detector when the X-rays having the second level of energy were radiated; and
successively generate a plurality of subtraction images in which the first site is rendered at a second frame rate higher than the first frame rate, wherein the processing unit generates one of the subtraction images by a first calculation using a first image and a second image generated next to the first image, and subsequently generates one of the subtraction images by a second calculation using the second image and a third image generated next to the second image, wherein the first and third images are the image of the first level of energy, and the second image is the image of the second level of energy.

* * * * *